United States Patent
Villarreal Suarez

(10) Patent No.: US 11,794,008 B2
(45) Date of Patent: Oct. 24, 2023

(54) SUPPORT DEVICES INCLUDING ELECTRICAL STIMULATION SYSTEMS AND METHODS FOR USING THE SAME

(71) Applicant: Toyota Motor North America, Inc., Plano, TX (US)

(72) Inventor: Dario Jose Villarreal Suarez, Farmers Branch, TX (US)

(73) Assignee: TOYOTA MOTOR NORTH AMERICA, INC., Plano, TX (US)

( * ) Notice: Subject to any disclaimer, the term of this patent is extended or adjusted under 35 U.S.C. 154(b) by 314 days.

(21) Appl. No.: 16/906,841

(22) Filed: Jun. 19, 2020

(65) Prior Publication Data

US 2021/0393953 A1 Dec. 23, 2021

(51) Int. Cl.
*A61N 1/36* (2006.01)
*A61G 5/04* (2013.01)
*B60R 16/03* (2006.01)

(52) U.S. Cl.
CPC ........... *A61N 1/36003* (2013.01); *A61G 5/04* (2013.01); *A61N 1/3603* (2017.08); *B60R 16/03* (2013.01)

(58) Field of Classification Search
CPC .......................... A61N 1/36003; A61N 1/3603
USPC ........................................................ 607/48
See application file for complete search history.

(56) References Cited

U.S. PATENT DOCUMENTS

| | | | |
|---|---|---|---|
| 4,421,336 A * | 12/1983 | Petrofsky | A61N 1/36003 74/105 |
| 5,022,385 A | 6/1991 | Harza | |
| 7,293,623 B2 | 11/2007 | Berkelmans | |
| 9,782,321 B1 * | 10/2017 | Semmens | A61N 1/0452 |

(Continued)

FOREIGN PATENT DOCUMENTS

| | | |
|---|---|---|
| DE | 8712851 U1 | 4/1988 |
| EP | 3510986 A1 | 7/2019 |

(Continued)

OTHER PUBLICATIONS

PCT/US2021/037746 Notification of Transmittal of The International Search Report and The Written Opinion of the International Searching Authority, or the Declaration dated Oct. 4, 2021.

(Continued)

*Primary Examiner* — Joseph M Dietrich
*Assistant Examiner* — Michael T. Holtzclaw
(74) *Attorney, Agent, or Firm* — DINSMORE & SHOHL LLP

(57) ABSTRACT

A support device includes a base portion structurally configured to support a user, one or more engagement members coupled to the base portion and engagable with a surface, a distance sensor, a power source electrically coupled to one or more electrical stimulation electrodes, and a controller communicatively coupled to the distance sensor and the power source, the controller including a processor and a non-transitory, processor-readable storage medium including a computer readable and executable instruction set, which, when executed, causes the processor to receive a (Continued)

signal from the distance sensor indicative of a detected distance traveled by the support device, and send a signal to the power source to engage the one or more electrical stimulation electrodes based at least in part on the detected distance traveled by the support device.

18 Claims, 5 Drawing Sheets

(56) References Cited

U.S. PATENT DOCUMENTS

| | | | | |
|---|---|---|---|---|
| 2013/0123568 | A1* | 5/2013 | Hamilton | A61N 2/02 600/13 |
| 2016/0075226 | A1 | 3/2016 | Biderman et al. | |
| 2016/0324713 | A1* | 11/2016 | Halperin | A61H 1/0262 |
| 2017/0231856 | A1* | 8/2017 | Karlovich | A63B 22/0235 607/148 |
| 2018/0280214 | A1* | 10/2018 | Ferguson-Pell | G01C 9/06 |
| 2018/0318583 | A1* | 11/2018 | McBride | A61N 1/0452 |
| 2019/0038484 | A1 | 2/2019 | Triolo et al. | |
| 2019/0192361 | A1* | 6/2019 | Sankai | A61G 5/04 |

FOREIGN PATENT DOCUMENTS

| | | |
|---|---|---|
| JP | 2003117006 A | 4/2003 |
| KR | 20120140442 A | 12/2012 |
| KR | 102041882 B1 | 11/2019 |

OTHER PUBLICATIONS

Functional electrical stimulation cycling wheelchair for stroke patients: design and preliminary evaluation results (http://www.jmbe.org.tw/files/648/public/648-2538-1-PB.pdf); accessed/published date Oct. 13, 2010.

* cited by examiner

SUPPORT DEVICES INCLUDING ELECTRICAL STIMULATION SYSTEMS AND METHODS FOR USING THE SAME

TECHNICAL FIELD

The present specification generally relates to support devices including electrical stimulation systems and methods for operating the same.

BACKGROUND

Support devices, such as wheelchairs and the like, are conventionally used to assist users in moving from one location to another. For example, wheelchairs may assist users that have limited or no use of their legs in moving between locations. However, the lack of use of a person's legs may lead to muscle atrophy and/or other undesirable outcomes.

SUMMARY

Support devices according to the present disclosure include electrical stimulation electrodes. In embodiments, the electrical stimulation electrodes may be engaged, thereby triggering contraction of the muscles of a user sitting within the support device. In embodiments described herein, engagement of the electrical stimulation electrodes may be based at least in part a distance traveled by the support device. By correlating the engagement of the electrical stimulation electrodes with the distance traveled by the support device, the electrical stimulation electrodes may cause the user's muscles to contract as if the user was walking the distance traveled by the support device. By contracting the user's muscles in this manner, support devices according to the present disclosure may assist in limiting muscle atrophy in the user's legs.

In one embodiment, a support device includes a base portion structurally configured to support a user, one or more engagement members coupled to the base portion and engagable with a surface, a distance sensor, a power source electrically coupled to one or more electrical stimulation electrodes, and a controller communicatively coupled to the distance sensor and the power source, the controller including a processor and a non-transitory, processor-readable storage medium including a computer readable and executable instruction set, which, when executed, causes the processor to receive a signal from the distance sensor indicative of a detected distance traveled by the support device, and send a signal to the power source to engage the one or more electrical stimulation electrodes based at least in part on the detected distance traveled by the support device.

In another embodiment, a method for operating a support device, the method includes moving the support device along a surface, where the support device includes a base portion structurally configured to support a user, and one or more wheels coupled to the base portion, detecting a distance traveled by the support device along the surface, and engaging one or more electrical stimulation electrodes based at least in part on the detected distance traveled by the support device.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments described herein are generally directed to support devices including electrical stimulation electrodes. The electrical stimulation electrodes, in embodiments, may be activated based at least in part on a distance traveled by the support device. By activating the electrical stimulation electrodes based at least in part on the distance traveled by the support device, a user's legs may be contracted in manner similar to if the user were to walk the distance traveled by the support device. By contracting the user's leg muscles in this way, muscle atrophy may be reduced as compared to support devices that do not stimulate and contract the user's leg muscles. These and other embodiments will now be described with reference to the appended figures.

As referred to herein, the phrase "communicatively coupled" refers to the interconnection of components of support devices described herein such that signals can be sent between the components, and may include, for example and without limitation, a wired connection, an optical connection, a wireless connection, or the like.

Figure 1:
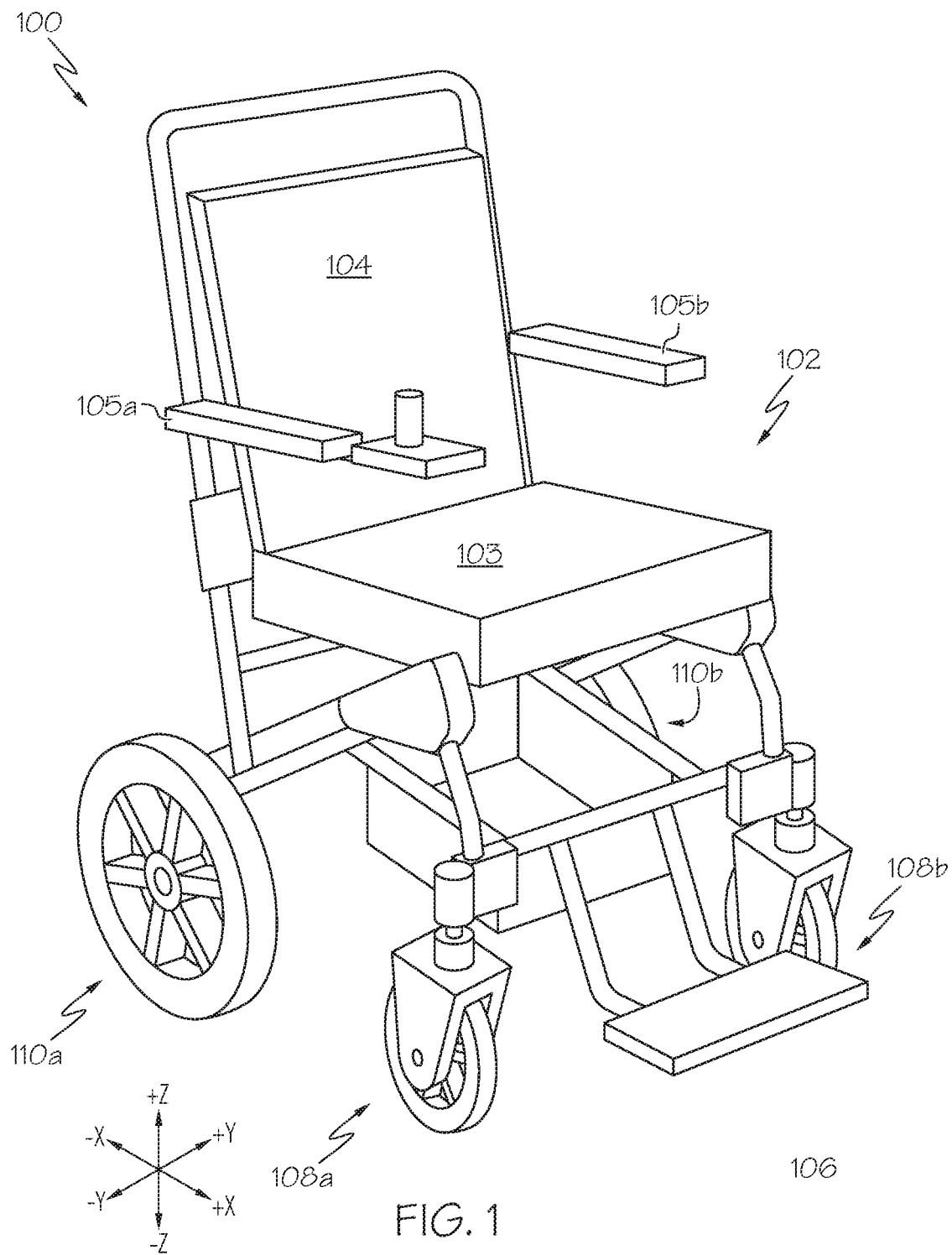
FIG. 1 schematically depicts a perspective view of a support device, according to one or more embodiments shown and described herein.

Referring initially to FIG. 1 a perspective view of a support device 100 is schematically depicted. In embodiments, the support device 100 includes a base portion 102 that is structurally configured to support a user. For example, in the embodiment depicted in FIG. 1, the base portion 102 includes a seat portion 103 and a back rest 104. In use, a user can sit on the seat portion 103 and may lean against the back rest 104. In some embodiments, the base portion 102 may further include one or more arm rests. For example, in the embodiment depicted in FIG. 1, the base portion 102 includes a first arm rest 105a and a second arm rest 105b that can support a user's arms.

In embodiments, the support device 100 includes one or more engagement members coupled to the base portion 102. The one or more engagement members are generally engagable with a surface, such as a floor or the ground. In the embodiment depicted in FIG. 1, the one or more engagement members are one or more wheels coupled to the base portion 102. For example, in the embodiment depicted in FIG. 1, the support device 100 includes a pair of front wheels 108a, 108b, and a pair of rear wheels 110a, 110b. The front wheels 108a, 108b, and the rear wheels 110a, 110b may "roll" along the surface to provide the support device 100 with mobility. While in the embodiment depicted in FIG. 1, the one or more engagement members include the front wheels 108a, 108b and the rear wheels 110a, 110b, it should be understood that the one or more engagement members may include any suitable construction suitable for moving the support device along a surface, for example and not limited to movable legs, tracks, or the like. Furthermore, while in the embodiment depicted in FIG. 1 includes the front wheels 108a, 108b and the rear wheels 110a, 110b, it should be understood that the support device 100 may include any suitable number of wheels, and may include more or fewer than the four wheels 108a, 108b, 110a, 110b depicted in the embodiment shown in FIG. 1.

In some embodiments, the support device 100 includes a foot rest 106 coupled to the base portion 102 that can be used to support a user's feet. In some embodiments, the support device 100 may include calf supports or the like positioned between the seat portion 103 and the foot rest 106 to support a user's legs.

Figure 2A:
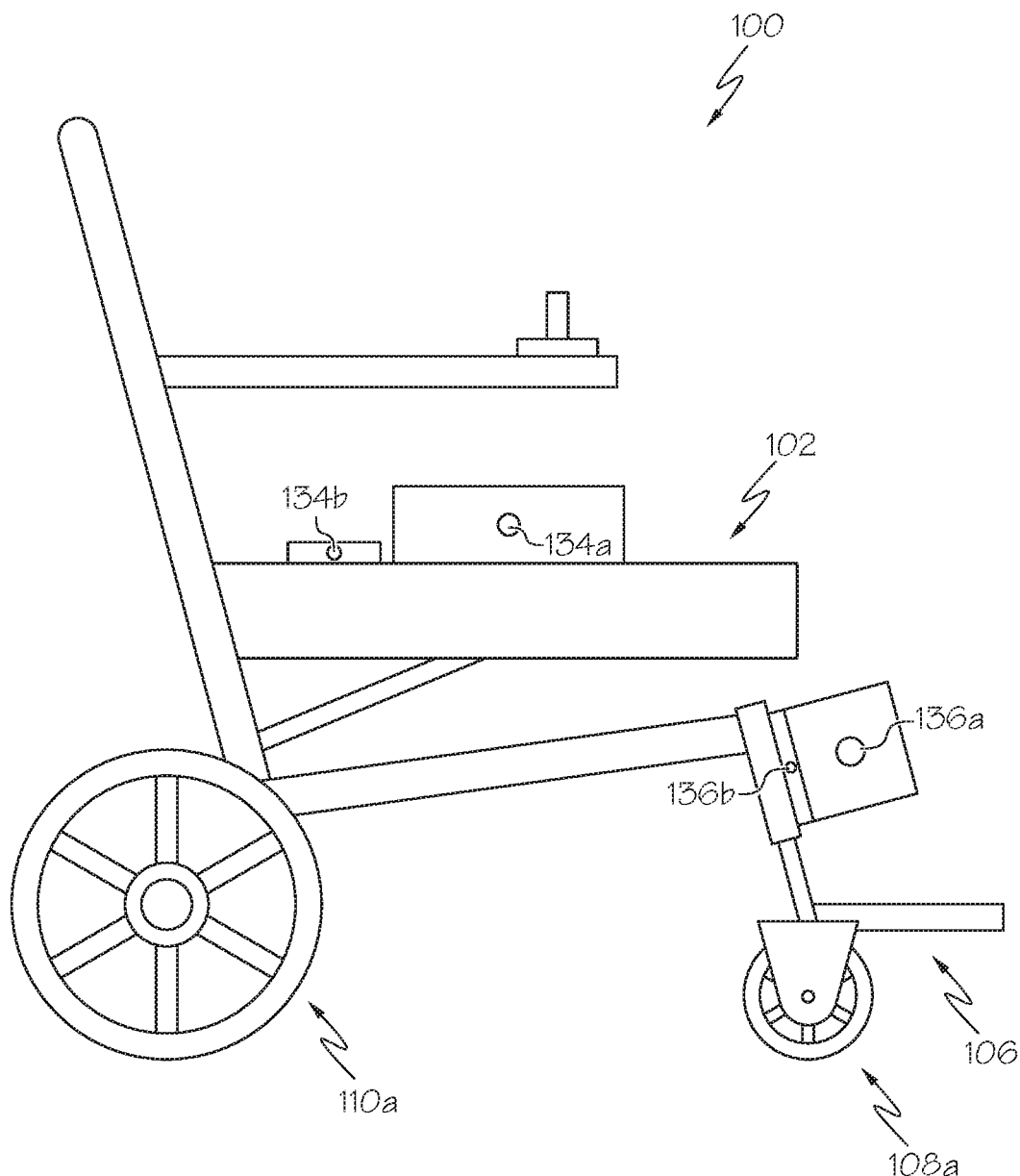
FIG. 2A schematically depicts a side view of the support device of FIG. 1, according to one or more embodiments shown and described herein.
Figure 2B:
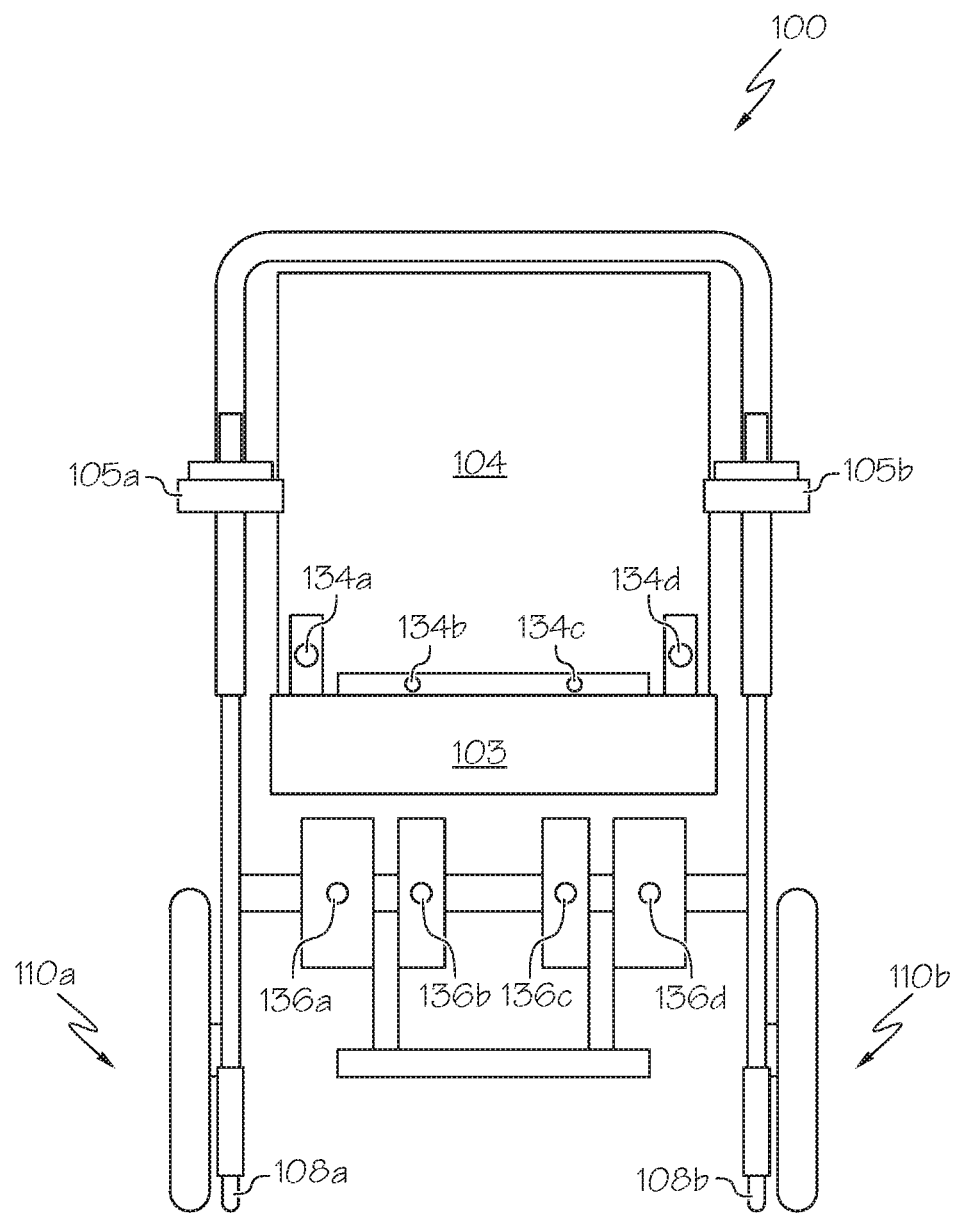
FIG. 2B schematically depicts a front view of the support device of FIG. 1, according to one or more embodiments shown and described herein.

Referring to FIGS. 2A and 2B, a side view and a front view of the support device 100 are schematically depicted, respectively. In some embodiments, the support device 100 includes one or more electrical stimulation electrodes. For example, in the embodiment depicted in FIGS. 2A and 2B, the support device 100 includes a first quadriceps electrical stimulation electrode 134a and a second quadriceps electrical stimulation electrode 134d. The first quadriceps electrical stimulation electrode 134a and the second quadriceps electrical stimulation electrode 134d are structurally configured to engage the quadriceps muscles of a user's legs, for example a user's left and right quadriceps. In some embodiments, the support device 100 includes a first glute electrical stimulation electrode 134b and a second glute electrical stimulation electrode 134c. The first glute electrical stimulation electrode 134b and the second glute electrical stimulation electrode 134c are structurally configured to engage the hamstring muscles (e.g., the gluteus maximus and/or biceps femoris muscles) of a user's legs (e.g., the user's right leg and left leg).

In some embodiments, the support device 100 includes a first tibia electrical stimulation electrode 136a and a second tibia electrical stimulation electrode 136d. The first tibia electrical stimulation electrode 136a and the second tibia electrical stimulation electrode 136d are structurally configured to engage the tibialis anterior muscles of a user's legs (e.g., the user's right leg and left leg). In some embodiments, the support device 100 further includes a first calf electrical stimulation electrode 136b and a second calf electrical stimulation electrode 136c. The first calf electrical stimulation electrode 136b and the second calf electrical stimulation electrode 136c are structurally configured to engage the calf muscles of a user's legs (e.g., the user's right leg and left leg).

While in the embodiment depicted in FIGS. 2A and 2B, the first and second quadriceps electrical stimulation electrodes 134a, 134d, the first and second glute electrical stimulation electrodes 134b, 134c, the first and second tibia electrical stimulation electrodes 136a, 136d, and the first and second calf electrical stimulation electrodes 136b, 136c, it should be understood that the support device 100 may include any suitable number of electrical stimulation electrodes that are structurally configured to engage muscles of a user's legs. Further, while the electrical stimulation electrodes 134a, 134b, 134c, 134d, 136a, 136b, 136c, 136d are depicted as being positioned on the base portion 102 of the support device 100, it should be understood that this is merely an example. In some embodiments, the electrical stimulation electrodes may be embedded in a fabric, garment or the like that is engaged with or worn by the user.

Figure 3:
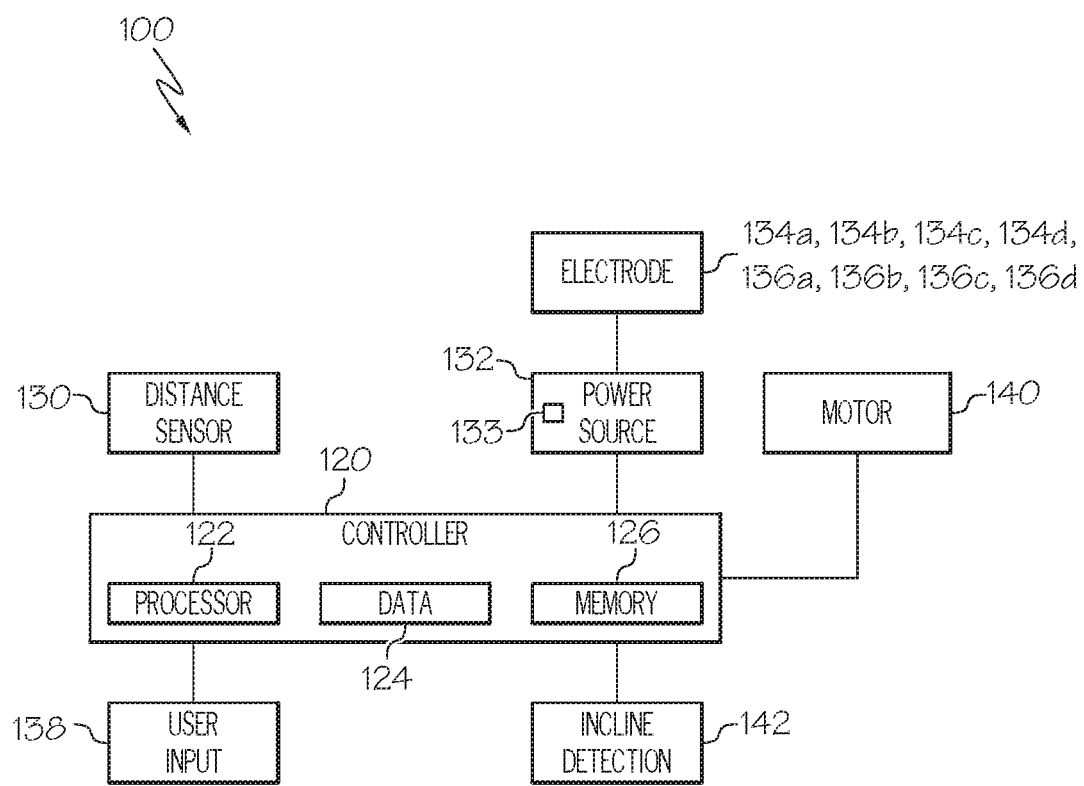
FIG. 3 schematically depicts a control diagram of the support device of FIG. 1, according to one or more embodiments shown and described herein.

Referring to FIG. 3, a control diagram for the support device 100 is schematically depicted. In embodiments, the support device 100 includes a controller 120. As illustrated, the controller 120 includes a processor 122, a data storage component 124, and/or a memory component 126. The memory component 126 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the controller 120 and/or external to the controller 120.

The memory component 126 may store operating logic, analysis logic, and communication logic in the form of one or more computer readable and executable instruction sets. The analysis logic and the communication logic may each include a plurality of different pieces of logic, each of which may be embodied as a computer program, firmware, and/or hardware, as an example. A local interface is also included in the controller 120, and may be implemented as a bus or other communication interface to facilitate communication among the components of the controller 120.

The processor 122 may include any processing component operable to receive and execute instructions (such as from a data storage component 124 and/or the memory component 126). It should be understood that while the components in FIG. 3 are illustrated as residing within the controller 120, this is merely an example, and in some embodiments, one or more of the components may reside external to the controller 120. It should also be understood that, while the controller 120 is illustrated as a single device, this is also merely an example.

In embodiments, the controller 120 is communicatively coupled to one or more components of the support device 100. For example, in the embodiment depicted in FIG. 3, the controller 120 is communicatively coupled to a distance sensor 130 and a power source 132. In some embodiments, the support device 100 further includes a user input 138, a motor 140, and/or an incline detection device 142 communicatively coupled to the controller 120.

In embodiments, the distance sensor 130 is structurally configured to detect a distance traveled by the support device 100. For example, in some embodiments, the distance sensor 130 may be an encoder or the like coupled to one or more of the wheels 108a, 108b, 110a, 110b (FIG. 2B). In embodiments, the distance sensor 130 is communicatively coupled to the controller 120 such that signals can be sent to and/or received from the controller 120. For example, in embodiments, the distance sensor 130 may send signals to the controller 120 indicative of a distance traveled by the support device 100, as described in greater detail herein. In some embodiments, activation of one or more of the electrical stimulation electrodes 134a, 134b, 134c, 134d, 136a, 136b, 136c, 136d is based at least in part on a detected distance traveled by the support device 100, as described in greater detail herein.

In embodiments, the power source 132 includes a device that is suitable to provide power to the electrical stimulation electrodes 134a, 134b, 134c, 134d, 136a, 136b, 136c, 136d. For example and without limitation, in embodiments the power source 132 may include a battery or the like that is electrically coupled to one or more of the electrical stimulation electrodes 134*a*, 134*b*, 134*c*, 134*d*, 136*a*, 136*b*, 136*c*, 136*d*. In some embodiments, the power source 132 may include an electrode controller 133 that is either internal or external to the power source 132. The electrode controller 133 may allow the power source 132 to selectively provide electrical power to the electrical stimulation electrodes 134*a*, 134*b*, 134*c*, 134*d*, 136*a*, 136*b*, 136*c*, 136*d*. For example, the electrode controller 133 of the power source 132 may receive signals from the controller 120 directing the power source 132 to selectively engage (e.g., provide electrical power) to one or more of the electrical stimulation electrodes 134*a*, 134*b*, 134*c*, 134*d*, 136*a*, 136*b*, 136*c*, 136*d*, as described in greater detail herein.

In embodiments, the user input 138 may include a device suitable to receive instructions and/or information from a user. For example, in embodiments, the user input 138 and may include an alpha-numeric keyboard, a graphical user interface (GUI), or the like. The user input 138 may send and/or receive signals to the controller 120, for example, the user input 138 may receive an input from a user, and may send signals to the controller 120 indicative of the received user input. In some embodiments, the user input 138 may also display information received from the controller 120 indicative of the operation of various components of the support device 100 (e.g., the power source 132, the motor 140, the incline detection device 142, etc.).

In embodiments, the incline detection device 142 is structurally configured to detect an orientation of the support device 100. For example in embodiments, the incline detection device 142 an orientation of the support device 100 about the Y-axis as depicted in FIG. 1. By detecting an orientation of the support device 100, the incline detection device 142 may detect whether the support device 100 is on an inclined surface (e.g., moving uphill) or on a declined surface (e.g., moving downhill). In embodiments, the incline detection device 142 may include any suitable device for detecting an orientation of the support device 100, and may include, for example and without limitation, a tilt sensor, a microelectromechanical system (MEMS) inclinometer, a pendulum-based inclinometer, a gyroscopic inclinometer, or the like. In embodiments, the incline detection device 142 is communicatively coupled to the controller 120, and may send signals to the controller 120 indicative of a detected incline of the support device 100, as described in greater detail herein.

In embodiments, the motor 140 may include a device suitable for providing the support device 100 with mobility. For example, in embodiments, the motor 140 may be coupled to one or more of the rear wheels 110*a*, 110*b* (FIG. 2B) and/or one or more of the front wheels 108*a*, 108*b* (FIG. 2B), and may be structurally configured to rotate one or more of the rear wheels 110*a*, 110*b* (FIG. 2B) and/or the front wheels 108*a*, 108*b* (FIG. 2B). For example and without limitation, the motor 140 may include a direct current (DC) motor, and alternating current (AC) motor, or the like. The motor 140 may be communicatively coupled to the controller 120 such that signals can be sent to and received from the controller 120. For example, the motor 140 may receive signals from the controller 120 directing the motor 140 to actuate, rotating one or more of the rear wheels 110*a*, 110*b* (FIG. 2B) and/or the front wheels 108*a*, 108*b* (FIG. 2B). In some embodiments, the motor 140 is electrically coupled to the power source 132 and the motor 140 may be powered by the power source 132.

Figure 4:
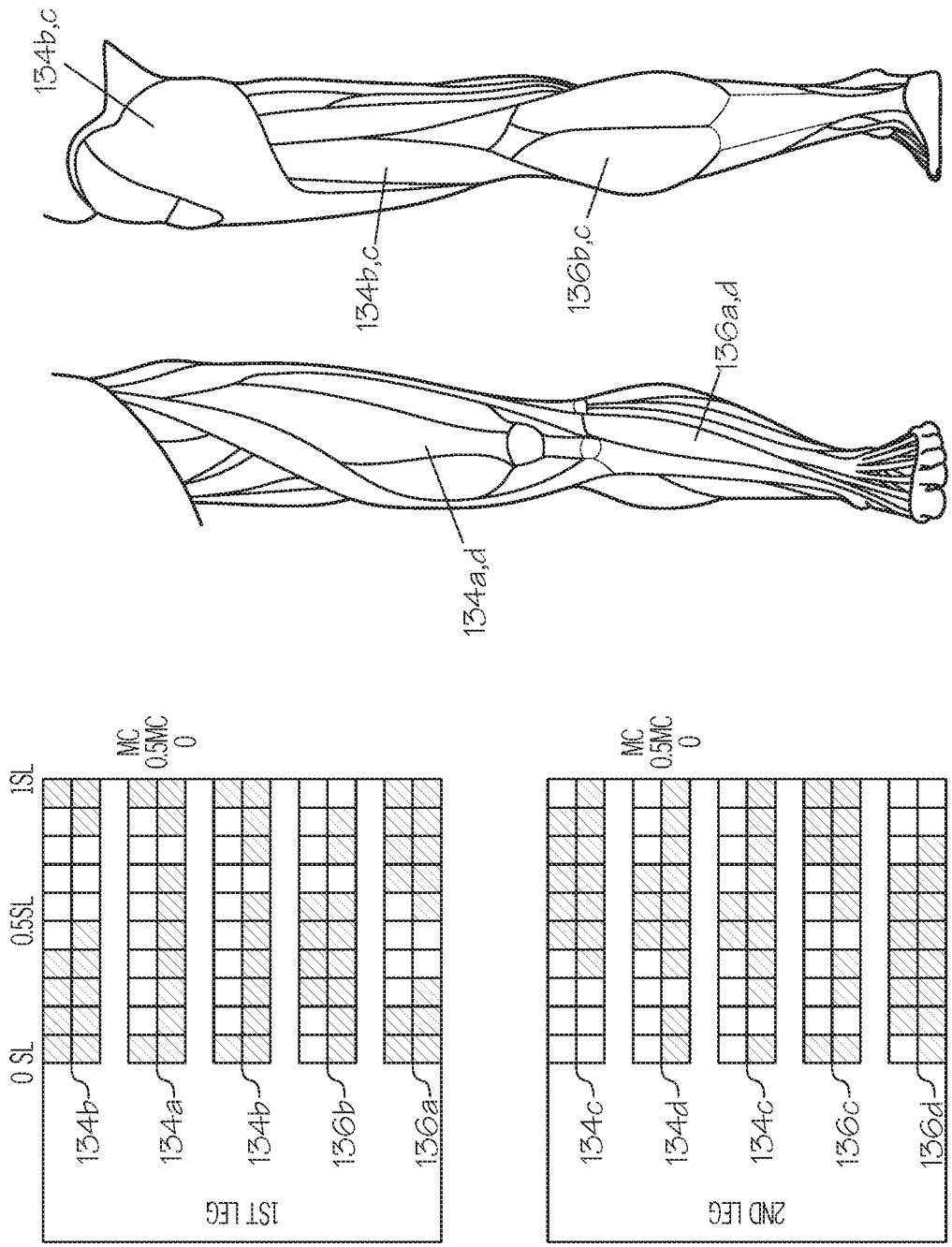
FIG. 4 schematically depicts an example electrode map for use with the support device of FIG. 1, according to one or more embodiments shown and described herein.

Referring to FIGS. 1, 3, and 4, example operation of the support device 100 will now be described. In embodiments, the controller 120 may receive a signal from the distance sensor 130 indicative of a distance traveled by the support device 100. The controller 120 may send a signal to the power source 132 to engage one or more of the electrical stimulation electrodes 134*a*, 134*b*, 134*c*, 134*d*, 136*a*, 136*b*, 136*c*, 136*d* based at least in part on the detected distance traveled by the support device 100. For example, in some embodiments, the greater the distance traveled by the support device 100, the greater number of times the one or more of the electrical stimulation electrodes 134*a*, 134*b*, 134*c*, 134*d*, 136*a*, 136*b*, 136*c*, 136*d* are engaged. However, in some embodiments, the lower the distance traveled by the support device 100, the fewer number of times the one or more of the electrical stimulation electrodes 134*a*, 134*b*, 134*c*, 134*d*, 136*a*, 136*b*, 136*c*, 136*d* are engaged. As one example, in some embodiments, the controller 120 may send a signal to the power source 132 to engage one or more of the electrical stimulation electrodes 134*a*, 134*b*, 134*c*, 134*d*, 136*a*, 136*b*, 136*c*, 136*d* in accordance with a determined number of strides that would have been taken by the user to travel the detected distance traveled by the support device 100.

For example, in some embodiments, the controller 120 may receive a signal indicative of an estimated stride length of a user. The controller 120 may receive a signal from the user input 138, for example, indicative of an estimated stride length of a user. In some embodiments, a user may input an estimated stride length via the user input 138. In some embodiments, a user may input characteristics from which an estimated stride length can be determined, for example, by the controller 120. As one example, a user may input a height of the user via the user input 138, and the controller 120 may determine an estimated stride length based at least in part on the input height of the user.

The controller 120 may determine a number of strides associated with the detected distance traveled by the support device 100, and may send a signal to the power source 132 to engage the one or more electrical stimulation electrodes 134*a*, 134*b*, 134*c*, 134*d*, 136*a*, 136*b*, 136*c*, 136*d* based at least in part on the determined number of strides.

In some embodiments, the controller 120 may direct the power source 132 to engage the one or more electrical stimulation electrodes 134*a*, 134*b*, 134*c*, 134*d*, 136*a*, 136*b*, 136*c*, 136*d* in an alternating manner to simulate a stride of the user. For example, in some embodiments, the controller 120 may send a signal to the power source 132 to engage a first electrical stimulation electrode 134*a*, 134*b*, 136*a*, 136*b*, where the first electrical stimulation electrode 134*a*, 134*b*, 136*a*, 136*b* is engaged with a first leg of the user. Subsequent to sending the signal to the power source 132 to engage the first electrical stimulation electrode 134*a*, 134*b*, 136*a*, 136*b*, the controller 120 may send a signal to the power source 132 to engage a second electrical stimulation electrode 134*c*, 134*d*, 136*c*, 136*d*, where the second electrical stimulation electrode 134*c*, 134*d*, 136*c*, 136*d* is engaged with a second leg of a user.

As one example and referring to FIGS. 2B, 3, and 4, in some embodiments, the controller 120 may direct the power source 132 to engage one or more electrical stimulation electrodes engaged with a first leg of the user. For example and as shown in FIG. 4, charts showing engagement timing and intensity of the one or more electrical stimulation electrodes 134*a*, 134*b*, 134*c*, 134*d*, 136*a*, 136*b*, 136*c*, 136*d* is depicted. In particular, the charts show the engagement timing as from the beginning of a stride "0SL" to the end of a stride "1SL," and shows the power level of the engagement of the one or more one or more electrical stimulation electrodes 134*a*, 134*b*, 134*c*, 134*d*, 136*a*, 136*b*, 136*c*, 136*d* ranging from "0" to "MC." As shown in FIG. 4, the first quadriceps electrical stimulation electrode 134a, the first glute electrical stimulation electrode 134b, the first tibia electrical stimulation electrode 136a, and/or the first calf electrical stimulation electrode 136b may be engaged. Subsequent to engaging the one or more of the electrodes engaged with the first leg of the user, the controller 120 may direct the power source 132 to engage one or more electrical stimulation electrodes engaged with the second leg of the user. For example, the second quadriceps electrical stimulation electrode 134d, the second glute electrical stimulation electrode 134c, the second tibia electrical stimulation electrode 136d, and/or the second calf electrical stimulation electrode 136c may be engaged.

As one example and as shown in FIG. 4, in some embodiments, a user's gluteus maximus muscle and/or hamstring in the user's first leg may contract upon the activation of the first glute electrical stimulation electrode 134b (FIG. 2B). Subsequent to the activation of the first glute electrical stimulation electrode 134b (FIG. 2B) a user's gluteus maximus muscle in the user's second leg may contract upon the activation of the second glute electrical stimulation electrode 134c (FIG. 2B). By alternately engaging electrical stimulation electrodes engaged with the first leg and the second leg of the user, the user's muscles may contract in a manner similar to a walking stride.

In some embodiments, the controller 120 may direct the power source 134 to engage the one or more electrical stimulation electrodes 134a, 134b, 134c, 134d, 136a, 136b, 136c, 136d at different power levels. Without being bound by theory, the power level (e.g., the electrical intensity) at which the one or more electrical stimulation electrodes 134a, 134b, 134c, 134d, 136a, 136b, 136c, 136d are engaged is associated with the intensity with which a user's muscles contract. For example, engaging the one or more of the electrical stimulation electrodes 134a, 134b, 134c, 134d, 136a, 136b, 136c, 136d with a comparatively high power level may cause a comparatively large muscle contraction, as compared to engaging the one or more of the electrical stimulation electrodes 134a, 134b, 134c, 134d, 136a, 136b, 136c, 136d with a comparatively low power level.

For example and referring to FIGS. 3 and 4 in some embodiments, the controller 120 sends a signal to the power source 132 to engage a first one of the one or more electrical stimulation electrodes 134a, 134b, 134c, 134d, 136a, 136b, 136c, 136d at a first power level. Subsequent to sending the signal to the power source 132 to engage the first one of the one or more electrical stimulation electrodes 134a, 134b, 134c, 134d, 136a, 136b, 136c, 136d at the first power level, the controller 120 may send a signal to the power source 132 to engage the first one of the one or more electrical stimulation electrodes 134a, 134b, 134c, 134d, 136a, 136b, 136c, 136d at a second power level that is different than the first power level.

As one example and referring to FIG. 4, in some embodiments, the controller 120 sends a signal to the power source 132 to engage the first glute electrical stimulation electrode 134b at a first power level at the beginning of the stride "0." Subsequent to engaging the first glute electrical stimulation electrode 134b at the first power level, the controller 120 sends a signal to the power source 132 to engage the first glute electrical stimulation electrode 134b at a second power level that is different than the first power level. For example and as shown in FIG. 4, in some embodiments, at mid-stride (e.g., 0.5SL), the first glute electrical stimulation electrode 134b is engaged at a power level 0.5 MC, as compared to the beginning of the stride "0," at which the first glute electrical stimulation electrode 134b is engaged at a power level MC that is greater than the power level 0.5 MC. As further shown in FIG. 4, each of the one of the one or more electrical stimulation electrodes 134a, 134b, 134c, 134d, 136a, 136b, 136c, 136d can be engaged at different power levels at different points in the stride, thereby varying the level of contraction of muscles in a manner similar to if the user were walking.

In some embodiments, the power level (e.g., the intensity of the engagement) of the one of the one or more electrical stimulation electrodes 134a, 134b, 134c, 134d, 136a, 136b, 136c, 136d is based at least in part on the detected incline of the support device 100, for example, as detected by the incline detection device 142. As one example, in response to receiving a signal from the incline detection device 142 that the support device 100 is on a positive incline (e.g., that the support device 100 is traveling uphill), the controller 120 may direct the power source 132 to engage the one or more of the electrical stimulation electrodes 134a, 134b, 134c, 134d, 136a, 136b, 136c, 136d at a comparatively high power level. In response to receiving a signal from the incline detection device 142 that the support device 100 is on a negative incline (e.g., that the support device 100 is traveling downhill), the controller 120 may direct the power source 132 to engage the one or more of the electrical stimulation electrodes 134a, 134b, 134c, 134d, 136a, 136b, 136c, 136d at a comparatively low power level, where the comparatively low intensity is lower than the comparatively high power level. In this way, the support device 100 may simulate the engagement of the user's muscles in accordance with the terrain (e.g., the incline or decline) traversed by the support device 100.

It should now be understood that embodiments described herein are directed to support devices including electrical stimulation electrodes. The electrical stimulation electrodes, in embodiments, may be activated based at least in part on a distance traveled by the support device. By activating the electrical stimulation electrodes based at least in part on the distance traveled by the support device, a user's legs may be contracted in manner similar to if the user were to walk the distance traveled by the support device. By contracting the user's leg muscles in this way, muscle atrophy may be reduced as compared to support devices that do not stimulate and contract the user's leg muscles.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the appended claims should be taken as the sole representation of the breadth of the present disclosure and the corresponding scope of the various embodiments described in this disclosure. Further, it should be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

It is noted that recitations herein of a component of the present disclosure being "structurally configured" in a particular way, to embody a particular property, or to function in a particular manner, are structural recitations, as opposed to recitations of intended use. More specifically, the references herein to the manner in which a component is "structurally configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "about" are utilized herein to represent the inherent degree of uncertainty that may be attributed to any quantitative comparison, value, measurement, or other representation. The terms "substantially" and "about" are also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A support device comprising:
   a base portion structurally configured to support a user;
   one or more engagement members coupled to the base portion and engagable with a surface;
   a distance sensor;
   a power source electrically coupled to one or more electrical stimulation electrodes; and
   a controller communicatively coupled to the distance sensor and the power source, the controller comprising a processor and a non-transitory, processor-readable storage medium comprising a computer readable and executable instruction set, which, when executed, causes the processor to:
      receive a signal from the distance sensor indicative of a detected distance traveled by the support device;
      determine a number of strides associated with the detected distance traveled by the support device; and
      send a signal to the power source to engage the one or more electrical stimulation electrodes to stimulate one or more muscles of the user based at least in part on the determined number of strides.

2. The support device of claim 1, wherein the one or more engagement members is one or more wheels coupled to the base portion.

3. The support device of claim 2, wherein the distance sensor is an encoder coupled to the one or more wheels.

4. The support device of claim 2, further comprising a motor coupled to the one or more wheels and electrically coupled to the power source.

5. The support device of claim 4, wherein the motor is communicatively coupled to the controller, and wherein the computer readable and executable instruction set, when executed, further causes the processor to direct the motor to rotate the one or more wheels.

6. The support device of claim 1, further comprising a user input communicatively coupled to the controller.

7. The support device of claim 6, wherein the computer readable and executable instruction set, when executed, further causes the processor to receive a signal from the user input indicative of an estimated stride length of the user, wherein the number of strides associated with the detected distance traveled by the support device is determined based on the estimated stride length.

8. The support device of claim 7, wherein the estimated stride length of the user is based at least in part on a height of the user.

9. The support device of claim 1, wherein the computer readable and executable instruction set, when executed, further causes the processor to:
   send a signal to the power source to engage a first electrical stimulation electrode of the one or more electrical stimulation electrodes, wherein the first electrical simulation electrode is engaged with a first leg of the user; and
   subsequent to sending the signal to the power source to engage the first electrical stimulation electrode, send a signal to the power source to engage a second electrical stimulation electrode of the one or more electrical stimulation electrodes, wherein the second electrical stimulation electrode is engaged with a second leg of the user.

10. The support device of claim 1, wherein the computer readable and executable instruction set, when executed, further causes the processor to:
    send a signal to the power source to engage a first electrical stimulation electrode of the one or more electrical stimulation electrodes at a first power level, wherein the first electrical simulation electrode is engaged with a first leg of the user; and
    subsequent to sending the signal to the power source to engage the first electrical stimulation electrode, send a signal to the power source to engage the first electrical stimulation electrode at a second power level that is different than the first power level.

11. The support device of claim 1, further comprising an incline detection device communicatively coupled to the controller.

12. The support device of claim 11, wherein the computer readable and executable instruction set, when executed, further causes the processor to:
    receive a signal from the incline detection device indicative of a detected incline of the support device, and wherein a power level of the engagement of the one or more electrical stimulation electrodes is based at least in part on detected incline of the support device.

13. A method for operating a support device, the method comprising:
    moving the support device along a surface, wherein the support device comprises a base portion structurally configured to support a user, and one or more wheels coupled to the base portion;
    detecting a distance traveled by the support device along the surface;
    determining a number of strides associated with the detected distance traveled by the support device; and
    engaging one or more electrical stimulation electrodes to stimulate one or more muscles of the user based at least in part on the determined number of strides.

14. The method of claim 13, wherein the determined number of strides is based at least in part on a height of the user.

15. The method of claim 13, further comprising:
engaging a first electrical stimulation electrode of the one or more electrical stimulation electrodes, wherein the first electrical simulation electrode is engaged with a first leg of the user; and
subsequent to engaging the first electrical stimulation electrode, engaging a second electrical stimulation electrode of the one or more electrical stimulation electrodes, wherein the second electrical stimulation electrode is engaged with a second leg of the user.

16. The method of claim 13, further comprising:
engaging a first electrical stimulation electrode of the one or more electrical stimulation electrodes at a first power level, wherein the first electrical simulation electrode is engaged with a first leg of the user; and
subsequent to engaging the first electrical stimulation electrode, engaging the first electrical stimulation electrode at a second power level that is different than the first power level.

17. The method of claim 13, further comprising detecting an incline of the support device, and wherein a power level of the engagement of the one or more electrical stimulation electrodes is based at least in part on detected incline of the support device.

18. The method of claim 17, further comprising increasing the power level of the engagement of the one or more electrical stimulation electrodes in response to detecting the support device is on an uphill incline.

\* \* \* \* \*